United States Patent [19]
Camus

[11] Patent Number: 5,755,694
[45] Date of Patent: May 26, 1998

[54] DEVICE FOR PROTECTING A HYPODERMIC NEEDLE

[75] Inventor: Michel Camus, Santes, France

[73] Assignee: B. Braun Celsa, Chasseneuil-Du-Poitou, France

[21] Appl. No.: 732,746

[22] Filed: Oct. 18, 1996

[30] Foreign Application Priority Data

Oct. 20, 1995 [FR] France ................ 95 12602

[51] Int. Cl.$^6$ ................................ A61M 5/00
[52] U.S. Cl. ............... 604/162; 604/171; 604/187
[58] Field of Search ..................... 604/198, 192, 604/263, 187, 110, 162, 171, 165

[56] References Cited

U.S. PATENT DOCUMENTS

| | | |
|---|---|---|
| 4,888,001 | 12/1989 | Schoenberg . |
| 4,998,922 | 3/1991 | Kuracina et al. . |
| 5,304,151 | 4/1994 | Kuracina . |

FOREIGN PATENT DOCUMENTS

| | | |
|---|---|---|
| 9108771 | 10/1991 | Germany . |
| 9001664 | 2/1992 | Netherlands . |

*Primary Examiner*—John D. Yasko
*Attorney, Agent, or Firm*—Rothwell, Figg, Ernst & Kurz

[57] ABSTRACT

The invention relates to a device for protecting a hypodermic needle comprising: a needle base disposed over a segment of the needle at the proximal end thereof, a needle portion shield comprising at least two generally flat wings having proximal and distal ends and being made of a flexible material, at least two hinges, with one said hinge connecting the proximal end of each said wing to said needle base, and a movable member having an axial opening therethrough at least partially delimited by generally flat surfaces, so as to be disposed over the wings along the axis of said needle portion, between upper and lower positions, wherein in the upper position, the movable member is above the hinges and in the lower position, the movable member is substantially at the distal end of the wings and its flat surfaces coact with an exterior surface of the wings to cause pivotally downward movement of the wings to draw them up to the needle portion along its axis when the movable member is moved from its upper to its lower position.

14 Claims, 5 Drawing Sheets

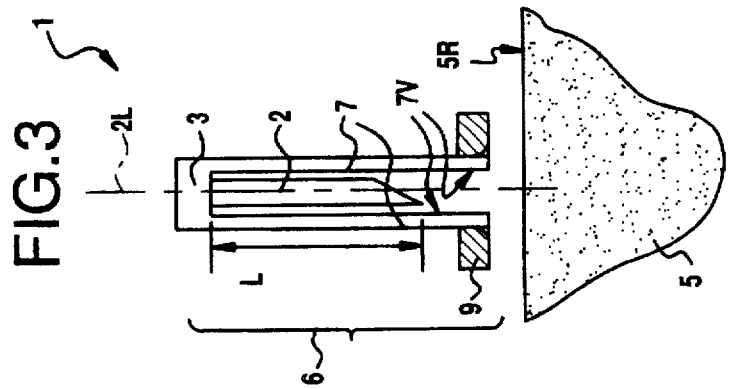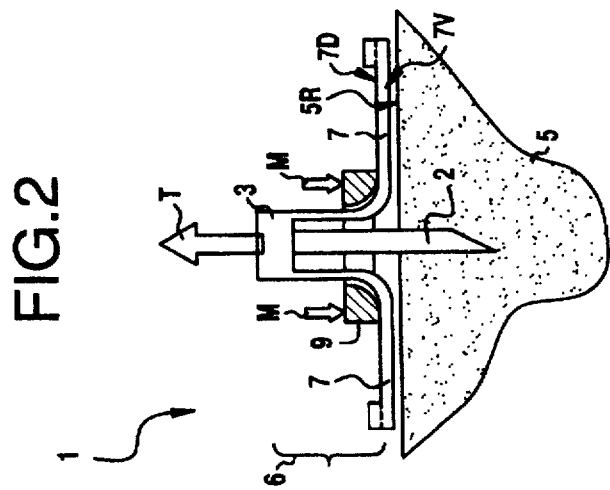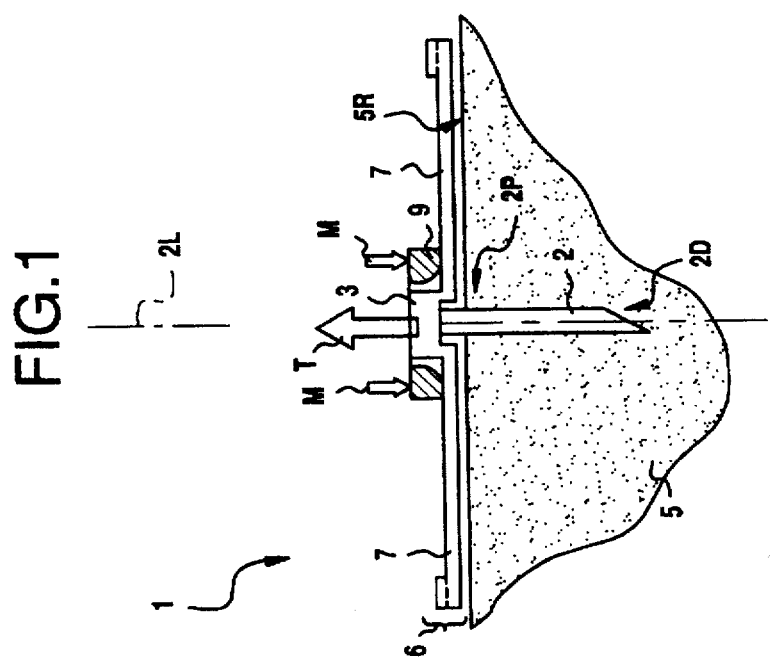

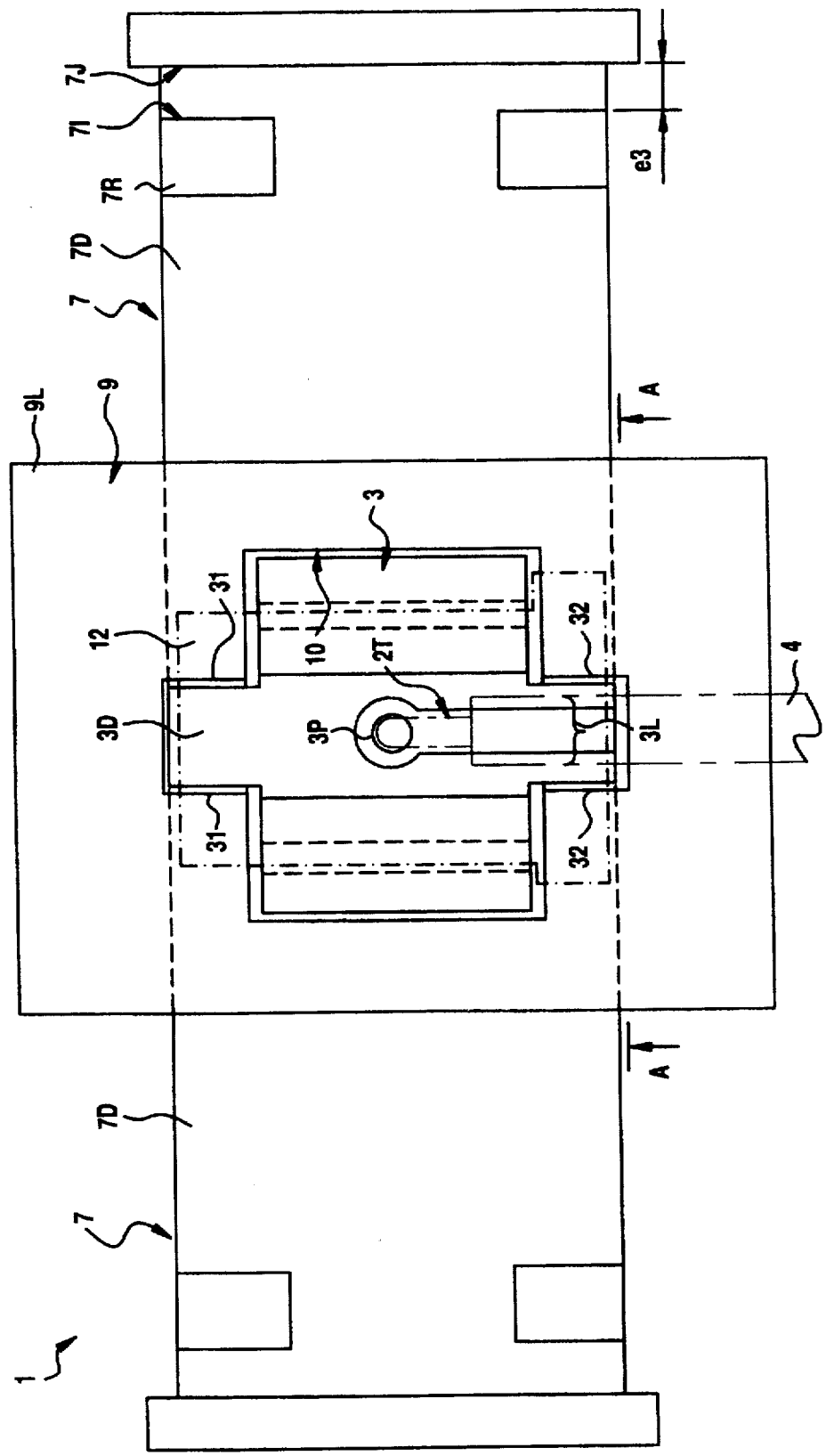

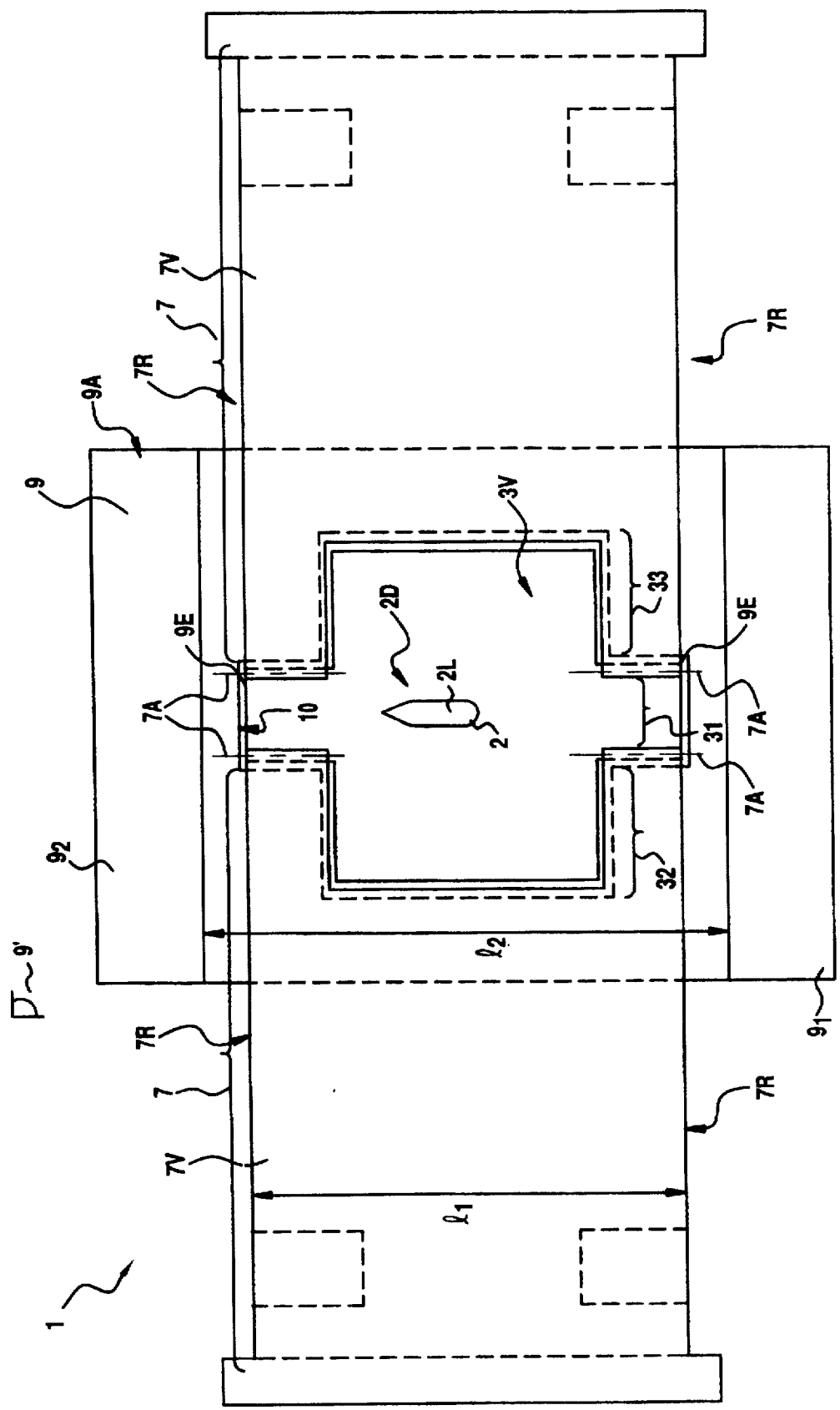

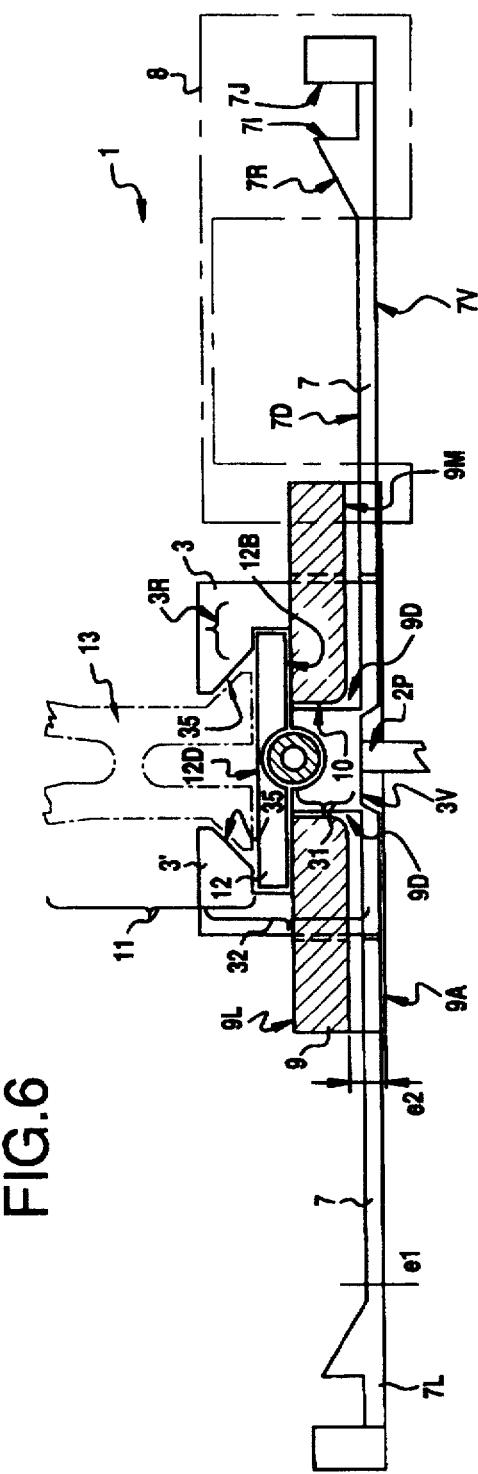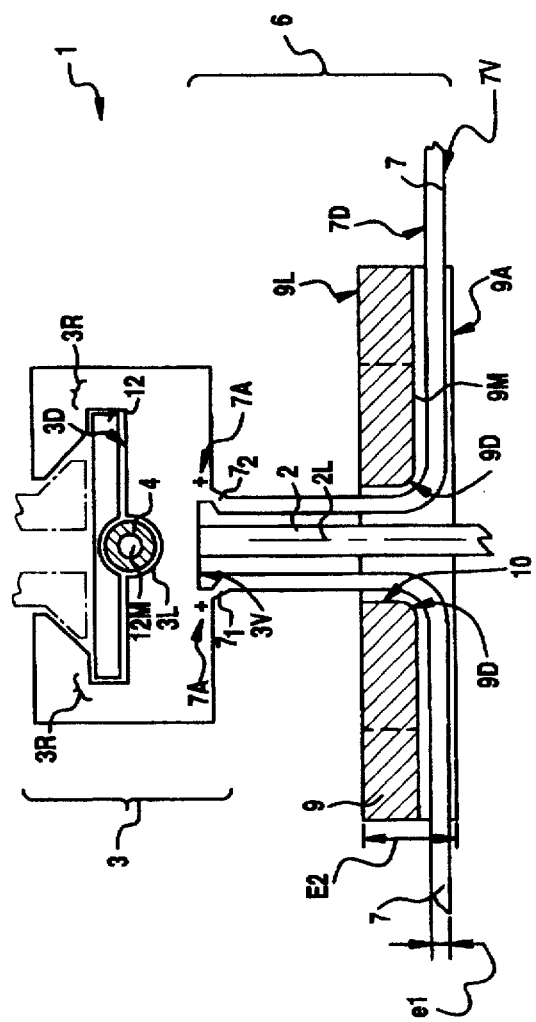
FIG.6
FIG.7

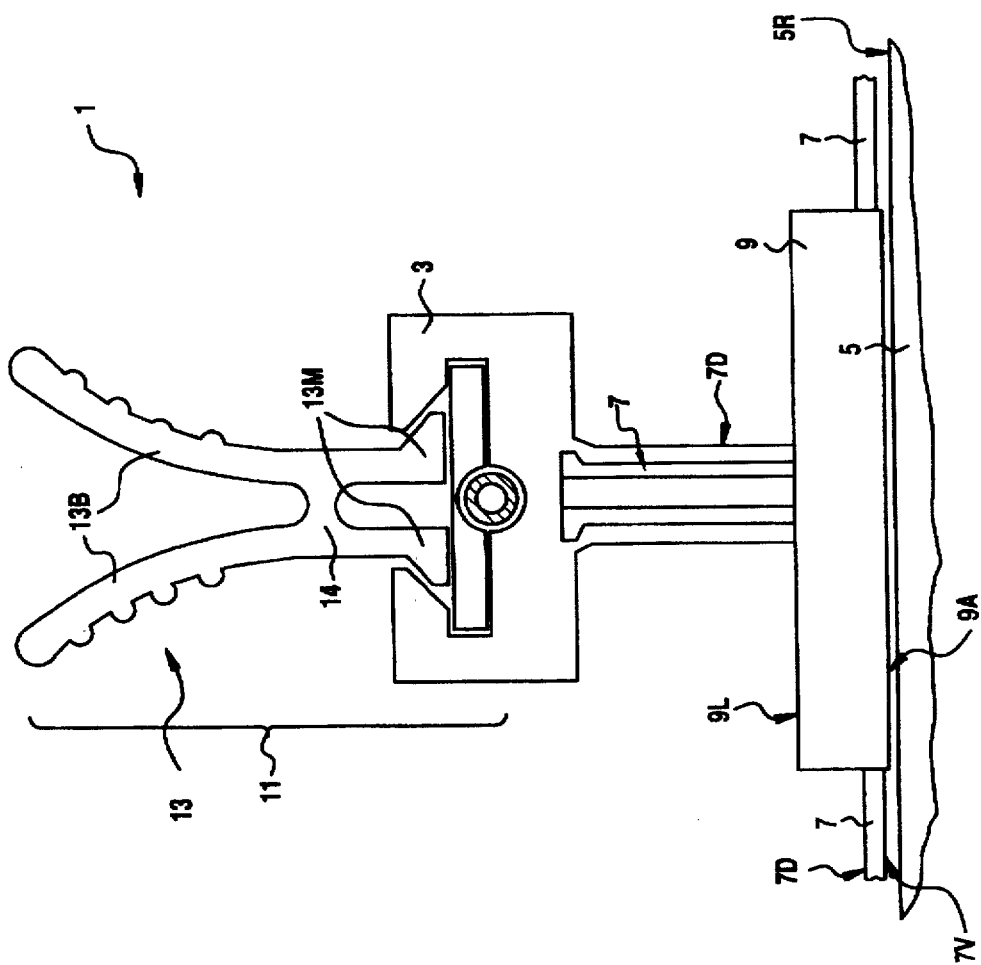

5,755,694

1

DEVICE FOR PROTECTING A HYPODERMIC NEEDLE

The invention relates to a device for protecting a hypodermic needle on an instrument comprising such a needle.

The invention can be applied to instruments that comprise a tubular needle having a perforating distal portion and a proximal portion that is to be connected to a duct for the circulation of a liquid.

The invention can be applied to instruments for injecting a liquid into a receiving medium, such as into an implanted site, and, equally well, to instruments for taking a liquid sample from a sampling medium.

The term "site" refers hereinafter to any medium into which the needle may be engaged.

The device of the invention is intended to prevent accidental jabs to persons handling these instruments.

Such accidents basically take place during the withdrawal of a needle from an injection medium or a sampling medium.

In order to reduce the probability of accidental jabs in the field of instruments equipped with a hypodermic needle, a very large number of devices are known which use at least one protection element which, being composed of rigid material and being associated at least indirectly with the proximal end of the needle, on the one hand, is movable between two positions in the first of which it largely disengages the needle in such a manner as to enable it to be used, and in the second of which it covers at least the distal end of the needle.

SCHOENBERG U.S. Pat. No. 4,888,001 relates to an instrument which has a hypodermic needle and which comprises such a protection device.

Although this device has its advantages, the applicant wishes to increase the safety, offered to users.

This is therefore the result the invention aims to achieve.

To that end, the invention relates to a hypodermic needle device comprising:

a needle having a portion adapted to be inserted into a body, said portion having a length along an axis and a distal sharp end and a proximal end, a needle base disposed over a segment of the needle at the proximal end of said needle portion, a needle portion shield comprising at least two generally flat wings having proximal and distal ends and being made of a flexible material, at least two hinges, with one said hinge connecting the proximal end of each said wing to said needle base, a movable member having an axial opening therethrough at least partially delimited by generally flat surfaces, so as to be disposed over the wings along the axis of said needle portion, between upper and lower positions, wherein in the upper position, the movable member is above the hinges and in the lower position, the movable member is substantially at the distal end of the wings and its flat surfaces coact with an exterior surface of the wings to cause pivotally downward movement of the wings to draw them up to the needle portion along its axis when the movable member is moved from its upper to its lower position.

Further, at least one of the following features is preferably provided on the device of the invention:

each wing has an interior surface opposite said exterior surface and which is free from any recess for containing the needle portion, so that in the lower position of the movable member, said needle portion remains

2 apparent between the wings and is not enclosed within the needle portion shield, the segment over which the needle base is disposed is bent, the movable member comprises (rounded) deviating abutments which are located below the flat surfaces of the movable member and against which the exterior surface of the wings is urged for coacting therewith when the movable member is moved between its lower and upper positions, the movable member is a pad generally flat in a general plane substantially perpendicular to the axis of the needle portion, the wings have a width and a thickness, the movable member has two lateral skids extending in the lower position of the movable element, substantially perpendicular to the axis of the needle portion and to the general plane of each wing, the distance between the skids is greater than the width of the wings, and the skids have a thickness which is greater than the thickness of the wings, so that the wings slide between the skids when the movable member is moved between its upper and lower positions, on their exterior surface, the wings have front and back protruding abutments located at their distal end, and the abutments have a distance therebetween, parallel to the axis of the needle portion, adapted for releasably locking therebetween the movable member in the lower position thereof, the needle base has (a) groove(s) extending perpendicular to the axis of the needle portion, the (each) groove has a length along said axis and an upper section longitudinally delimited by lateral flanges, and the device further comprises a removable handle having proximal and distal ends, said distal end being engaged into the groove(s), below the upper flanges, the removable handle has two articulated distal jaws integral with two operating branches, the jaws being engaged within the groove(s) of the needle base when the handle is disposed therein, the needle base further comprises an abutment plate disposed within the groove(s), below the removable handle, the plate having dimensions adapted for coacting in an abutting relationship with the movable members when in its upper position.

The invention will be understood well with the aid of the following description which is given by way of non-limiting example with reference to the appended drawings in which:

FIGS. 1 to 3 are three partially sectional views, along a plane perpendicular to a receiving surface against which it is used, of an instrument equipped with the device according to the invention in different configurations between a state in which the needle is implanted and a state in which it is protected by the elements provided for the purpose;

FIG. 4 is a plan view of an instrument equipped with the device according to the invention;

FIG. 5 is a bottom view of an instrument equipped with the device according to the invention;

FIGS. 6 and 7 are two sectional views along A—A of the instrument of FIG. 4;

FIG. 8 is a side view of the member for gripping the instrument according to the invention.

The drawings show an instrument 1 which uses a hypodermic needle 2 which comprises a perforating (or sharp) distal portion 2D and a proximal portion 2P and which, carried by the needle base 3 of the instrument 1, is connected at least indirectly to a duct 4 for the circulation of a liquid (not shown).

For example, the instrument 1 is an instrument for injecting a liquid into an injection medium 5 located under a surface 5R referred to as the receiving surface.

By way, of example, the medium 5 comprises a site 5 implanted under a receiving surface 5R, such as the skin of a patient (not shown).

The distal end 2D of the needle 2 advantageously has a "HUBER" chamfer, but this is not to be interpreted as a limitation.

As illustrated in the drawings, the portion of the needle, 2, to be axially inserted in the body 5, is approximately at right-angles to the receiving surface 5R in which it is engaged, but this is not to be interpreted as a limitation.

At a chosen moment during the use of the instrument 1, the hypodermic needle 2 has to be withdrawn from the medium 5 in which it is implanted.

This withdrawal is effected by manual action on the hypodermic instrument 1 of which the body 3 has, for the purpose, at least one surface 3S, 3D, 12B for at least indirect gripping.

The instrument 1 comprises, integral with the body 3 on which the needle 2 is held by its proximal end 2P in such a manner that it extends substantially at right-angles to one of the faces 3V, referred to as the ventral face, of the body 3, a needle shield 6 which is constituted by:

two generally flat symmetrical wings 7 which can be moved relative to the needle base 3 about axes 7A substantially parallel to a direction intersecting the longitudinal axis 2L of the needle 2 in such a manner that they can be placed in at least two functionally distinct configurations, viz.

one configuration, referred to as the protection configuration, in which they each have a face 7V, referred to as the ventral face, extending along the needle 2, and one configuration, referred to as the use configuration, in which they each, especially, have their ventral face 7V spaced away from the needle 2, a means 8 for locking the elements 7 in the protection configuration.

For the articulation of the wings, two hinges $7_1$, $7_2$ are provided, with one said hinge integrally connecting the proximal end of each wing 7 to the needle base 3.

As shown in the drawings, each flat wing 7 comprises two opposing faces 7V, 7D, viz., on the one hand, one face, referred to as the ventral face 7V, which is to be supported on a receiving surface 5R, such as the skin, in which the hypodermic needle 2 is engaged and, on the other hand, one face 7D, referred to as the dorsal face, on which an action for applying the instrument 1 against the receiving surface 5R, or indeed an action for applying the wings 7 against the hypodermic needle 2, can be exerted.

The interior surface 7V is exclusively flat.

It is noteworthy that:

the generally flat symmetrical wings 7 are each formed by a flexible plate 7 of determined flexibility, at least one movable element or member 9 co-operates with the wings 7 and, when it is moved towards the receiving surface 5R, while the needle 2 is withdraw n therefrom, ensures the progressive application of each plate 7 against the needle 2, that is to say, the application against the needle 2 of any portion of the flexible plate 7 which extends between the body 3, or base, of the instrument 1 and the receiving surface 5R from which the needle 2 is withdrawn, the application taking place gradually as the needle is being withdrawn.

Referring to the drawings, it can be seen that the application takes place from the proximal end 2P of the needle 2 towards its distal end 2D.

As mentioned, the application of the plates 7 is carried out gradually in the course of the withdrawal of the needle 2 from the receiving surface 5R.

The safety of use of an instrument equipped with the device according to the invention is therefore especially increased.

The plates 7 each have a longitudinal dimension greater than the length L of the needle 2.

It is noteworthy that the movable member 9 comprises at least two abutments 9D which, referred to as deflecting abutments, are arranged so that they are each Supported at least locally against the dorsal face 7D of a plate 7 and, during the withdrawal of the needle 2 from the medium 5 located under the receiving surface 5R, enable the dorsal surface 7D to slide and, in the manner of a pulley, bring about the bending and deflection of the plate 7 between, on the one hand, the support plane it finds against the receiving surface 5R and, on the other hand, a direction substantially parallel to the withdrawal direction of the needle 2.

The abutments are integral with the base 3 and located just below flat surfaces $3_1$, $3_2$ of the needle base which locally delimit the opening 10 provided through said base for the passage of the wings 7.

Advantageously, but this is not to be interpreted as a limitation, such abutments 9D are formed by rounded surfaces.

The presence of the movable member 9 further increases the safety of use of the instrument equipped with the device 6 of the invention.

Each plate or wing 7 is composed of a material of a nature and thickness e1 such that:

its flexibility allows it to slide against a deflecting abutment 9D, with deflection at least at right-angles, without impairment to the plate 7, despite this flexibility, the thickness of the plate 7 is at least sufficient to resist tearing caused by pronounced lateral application against the distal end 2D of the needle 2.

The person skilled in the art is capable of choosing the appropriate material and thickness.

It will be noted that the protection screen constituted by each plate 7 is surprisingly formed from a flexible material.

It is noteworthy that the movable member 9 has a general flat shape in a general plane 9' perpendicular to the axis 2L of the needle. It comprises, in its face to be supported against the receiving surface 5R, recesses 9E for accommodating the plates 7 in accordance with their thickness e1 when the instrument 1 is in the configuration referred to as the use configuration.

The recesses 9E are especially delimited by a face 9M substantially parallel to the face 9A to be supported on the receiving surface 5R.

More precisely, the movable member 9 is presently a generally flat and rectangular pad comprising (on its lower surface) two lateral protruding skids $9_1$, $9_2$ (FIG. 5) extending perpendicular to the axis 2L. The width $I_2$ between the skids is greater than the width $I_1$ of each wing. It is the same for the thickness ($e_2$, $e_1$, respectively; FIG. 6).

As a result, the movable member 9 remains supported on the receiving surface 5R during the withdrawal of the needle 2, while the wings are sliding between the skids.

In order to withdraw the hypodermic needle, it is sufficient to maintain the movable member 9 pressed downwardly against the receiving surface 5R, especially by at least an action M, while at least a traction action T is exerted on the body 3 of the instrument 1.

The plates 7 slide against the receiving surface 5R and against the deflecting abutments 9D in order, under the effect of the deflecting abutments, to be applied against the portion of needle 2 withdrawn from the receiving surface 5R.

It is noteworthy that:

the movable member 9 is a substantially flat member, of determined overall thickness E2, comprising two opposing faces 9A, 9L, viz. one face 9A, referred to as the support face because it is to be supported at least locally against the receiving surface 5R, and one face 9L, referred to as the free face, which is to receive an application action towards that receiving surface 5R, formed in the thickness E2 of that member 9, a slot 10, on the one hand, at the edge of which the deflecting abutments 9D are arranged, and, on the other hand, of which the cross-section has a shape and an extent at least sufficient to permit the engagement of each portion of the plates 7 placed in such a manner that they are supported against one another, after deflection by the abutments 9D provided for the purpose, the needle base 3 of the instrument 1 has, recessed relative to its ventral face 3V, at least one portion 31, 32, 33, referred to as the first portion (31), which, having a cross-section at least equivalent to that of the assembly constituted by the plates 7 when they are joined at least locally against the needle 2, is to co-operate in sliding manner with the slot 10 in order to carry the plates 7 in the area of the support face 9A of the movable member 9, each with its dorsal face 7D supported locally against a deflecting abutment 9D of that movable member 9, and to have beyond a face 3D of the body 3 which, referred to as the dorsal face, is arranged opposite its ventral face 3V, at least one means 11 for gripping the body 3, and at least one abutment 12B for support against at least one face 9L of the movable member 9 arranged opposite its support face 9A, in such a manner as to obstruct the disengagement of the member 9, the wings 7 each carry in the area of their free distal end 7L, that is to say, in the area of their end 7L arranged opposite that connected to the body 3, protruding front and back abutments 7I, 7J which face one another and which are formed on the exterior surface of the wings to co-operate with the surfaces 9A, 9M of the movable member 9 to constitute the means 8 for releasably locking the plates 7 in a state of support against the needle 2 (lower position of the movable member).

The distance $e_3$ between the front and back abutments 7I, 7J is substantially egal to the distance $E_2-e_2$ ($E_2$: overall thickness of the pad 9; $e_2$: thickness of the central recess of the pad, between the skids $9_1$, $9_2$).

Associated with at least some of the abutments 7I carried by the plates 7 in order to immobilise the movable member 9 are ramps 7R which are to co-operate with the movable member 9 for the purpose of deforming resiliently and at least locally at least one of the member 9 and the plates 7, in such a manner that, after crossing the ramps, the resilient return of the deformed portions causes the opposing abutments to be locked.

The expression "cross-section of the slot 10" refers to its section in a plane at right-angles to its longitudinal axis, that is to say, to the imaginary axis it has along the thickness of the movable member 9.

The expression "cross-section of the body 3" refers to its section in the same plane as that of the cross-section of the slot 10.

Preferably, but this it not to be interpreted as a limitation, the face 9L that is to co-operate with the abutment 12B opposing the disengagement of the needle base 3 is the face 9L referred to as the free face of the movable member 9.

It is noteworthy that the abutment 12B opposing the disengagement of the body 3 is carried by the body 3 in such a manner that it is movable between two positions, viz., on the one hand, a first position in which it is moved away to enable the body 3 to be mounted in the slot 10 of the movable member 9 and, on the other hand, a second position in which it is located opposite the free face 9L carried by the movable member 9 so that it opposes the disengagement of the body 3.

In a manner which is also noteworthy, the abutment 12B opposing the disengagement of the body 3 is carried by a member 12 which, being separate from the needle base 3, is slidably mounted in at least one groove 3R formed in the needle base 3, in such a manner as to translate into a plane which is approximately perpendicular to the needle 2 (axis 2L).

The member 12 is substantially flat and has two opposite faces 12B, 12D. The dimensions of such a plate are adapted for coacting (in an abutment relationship) with the pad 9 when in its upper position (FIGS. 1 and 6).

Once mounted on the needle base 3, the abutment plate 12 is immobilised by any suitable means, for example, by means of an adhesive.

The needle 2 is secured to the needle base 3 by its proximal end 2P and, at that end 2P, it is bent substantially at right-angles so that it has a portion 2T for connection to a duct 4 substantially parallel to the receiving surface 5R.

Notably:

the body 3 comprises, on the one hand, an axial perforation 3P for the passage of the needle 2 between its face 3V referred to as the ventral face and an opposite face 3D referred to as the dorsal face and, on the other hand, formed in the dorsal face 3D, an area 3L for supporting at least indirectly and for accommodating at least a section of the connecting portion 2T, the sliding member 12 is constructed not only in such a manner that it comprises the abutment 12B obstructing the removal of the body 3 and the movable member 9, but also in such a manner that it comprises an abutment 12M for holding the connecting portion 2T of the needle against the area 3L of the body 3 receiving it.

Likewise, the sliding member 12 is designed in the manner of a hood which covers the connecting portion 2T and the support area 3L.

It is noteworthy that the body 3 comprises two grooves 3R arranged to guide the sliding of the member 12 with its abutment 12M for maintaining the portion 2T in a plane parallel to the dorsal face 3D of the body 3.

Advantageously, the means 11 for gripping the body 1A comprises:

on the one hand, separate from the instrument 1, a removable handle 13 for gripping with the fingers in order to manipulate the instrument to enable at least one of the operations of introducing or withdrawing the hypodermic needle 2 to be effected, on the other hand, integral with the body 3, at least two abutments 3S, 3D, 12D arranged in such a manner as to enable the member 13 for gripping with the fingers to be secured in a releasable manner.

The abutments 3S are defined by lateral flanges 3',3" extending above the groove(s), so as to define the upper section thereof.

The member 13 for gripping with the fingers is advantageously a pair of pliers.

Notably:
- the grooves 3R for gliding the sliding member 12 are arranged one on each side of a central plane of the plates 6, and
- the abutments 3S, 3D, 12D for gripping the body 3 are arranged above the grooves 3R when the instrument 1 is observed with the needle orientated vertically and downwards.

Notably, the handle 13 is a pair of pliers comprising two jaws 13M and two operating branches 13B, each of which is integrally connected to one of the jaws 13M and articulated about an integral hinge 14.

Further:
- the jaws 13M have surfaces arranged to co-operate with the abutments 3S, 3D, 12D for gripping the body 3 of the instrument,
- the jaws 13M and the branches 13B are articulated in such a manner that an action moving the branches 13B towards one another induces an action moving the jaws 13M away from one another.

Notably:
- apart from a first portion 31, on the one hand, of which the cross-section has a shape and extent at least sufficient to permit the engagement of each portion of the plates 7 placed so that they are supported against one another, after deflection bar the deflecting abutments 9D, and, on the other hand, which extends between the ventral and dorsal faces 3V, 3D of the body 3, the body 3 comprises:
  - a second 32 and a third portion 33 which, on the one hand, each extending at least between the plane of the ventral 3V and dorsal 3D faces of the body, project laterally on each side of the first portion 31 in such a manner that they carry, above the plane of the face 3D referred to as the dorsal face of the body 3 and on each side of a central plane of the plates 6, the abutments 3S, 12S which are to grip the body 3,
- the slot 10 of the movable member 9 has a cross-section adjusted to that of the body 3 in such a manner as to permit sliding on the body 3.

In a notable embodiment, on the one hand, the slot 10 of the movable member 9 and the body 3 which carries the needle 2 have a cruciform cross-section and, on the other hand, the movable member 9 carries two groups of two opposing deflecting abutments 9D and those groups are arranged in such a manner that their abutments co-operate with the dorsal faces 7D of the plates 7 substantially in the area of the edges 7R which delimit them laterally.

I claim:

1. A hypodermic needle comprising:
   a needle having a portion adapted to be inserted into a body through a receiving surface thereof, said portion having a length along an axis and a distal sharp end and a proximal end,
   a needle base disposed over a segment of the needle at the proximal end of said needle portion,
   a needle portion shield comprising at least two generally flat and flexible wings having proximal and distal ends,
   at least two hinges, with one said hinge connecting the proximal end of each said wing with said needle base, and
   a movable member having an axial opening therethrough at least partially delimited by generally flat surfaces, so as to be disposed over the wings along the axis of said needle portion, between upper and lower positions,
   wherein in the upper position, the movable member is above the hinges and in the lower position, the movable member is substantially at the distal end of the wings and its flat surfaces coact with an exterior surface of the wings to cause pivotally downward movement of the wings to draw them up to the needle portion along its axis while bending said wings when the movable member is pressed on the receiving surface and is moved from the upper position to the lower position, for withdrawing the needle portion from the body after being inserted therein.

2. The device according to claim 1, wherein each wing has an interior surface opposite said exterior surface and which is free from any recess for containing the needle portion, so that in the lower position of the movable member, said needle portion remains apparent between the wings and is not enclosed within the needle portion shield.

3. The device according to claim 1, wherein the segment over which the needle base is disposed is bent.

4. The device according to claim 1, wherein the movable element comprises rounded deflecting abutments which are located below the flat below the flat surfaces of the movable member and against which the exterior surface of the wings is urged for coacting therewith when the movable member is moved between its lower and upper positions.

5. The device according to claim 1, wherein the movable member is a pad generally flat in a general plane substantially perpendicular to the axis of the needle portion.

6. The device according to claim 1, wherein:
   the wings have a width and a thickness,
   the movable element has two lateral skids extending substantially perpendicular to the axis of the needle portion and to the general plane of each wing, in the lower position of the movable element,
   the distance between the skids is greater than the width of the wings, and
   the skids have a thickness which is greater than the thickness of the wings,
   so that the wings slide between the skids when the movable member is moved between its upper and lower positions.

7. The device according to claim 1, wherein on their exterior surface the wings have front and back protruding abutments located at their distal end, and the abutments have a distance therebetween, parallel to the axis of the needle portion, adapted for releasably locking therebetween the movable member in the lower position thereof.

8. The device according to claim 1, wherein
   the needle base has a groove extending perpendicular to the axis of the needle portion,
   the groove has a length along said axis and an upper section longitudinally delimited by lateral flanges,
   and the device further comprises a removable handle having proximal and distal ends, said distal end being engaged into the groove, below the upper flanges.

9. The device according to claim 8, wherein the removable handle has two articulated distal jaws integral with two operating branches, the jaws being engaged within the groove of the needle base when the handle is disposed therein.

10. The device according to claim 8, wherein the needle base further comprises an abutment plate disposed within the groove, below the removable handle, the plate having dimensions adapted for coacting in an abutting relationship with the movable member when in its upper position.

11. A hypodermic needle device comprising:
    a needle having a portion adapted to be inserted into a body, said portion having a length along an axis and a distal sharp end and a proximal end, a needle base disposed over a segment of the needle at the proximal end of said needle portion, a needle portion shield comprising at least two generally flat wings having proximal and distal ends and being made of a flexible material, at least two hinges, with one said hinge connecting the proximal end of each said wing with said needle base, a movable member having an axial opening therethrough at least partially delimited by generally flat surfaces, so as to be disposed over the wings along the axis of said needle portion, between upper and lower positions, wherein in the upper position, the movable member is above the hinges and in the lower position, the movable member is substantially at the distal end of the wings and its flat surfaces coact with an exterior surface of the wings to cause pivotally downward movement of the wings to draw them up to the needle portion along its axis, when the movable member is moved from the upper position to the lower position, and wherein:

the wings have a width and a thickness, the movable element has two lateral skids extending substantially perpendicular to the axis of the needle portion and to the general plane of each wing, in the lower position of the movable element, the distance between the skids is greater than the thickness of the wings, and the skids have a thickness which is greater than the thickness of the wings, so that the wings are engaged between the skids when the movable element is moved between its upper and lower positions.

12. A hypodermic needle device comprising:

a needle having a portion adapted to be inserted into a body, said portion having a length along an axis and a distal sharp end and a proximal end, a needle base disposed over a segment of the needle at the proximal end of said needle portion, needle portion shield comprising at least two generally flat wings having proximal and distal ends, at least two hinges, with one said hinge connecting the proximal end of each said wing with said needle base, a movable member having an axial opening therethrough at least partially delimited by generally flat surface, so as to be disposed over the wings along the axis of said needle portion, between upper and lower positions, wherein in the upper position, the movable member is above the hinges in the lower position, the movable member is substantially at the distal end of the wings and its flat surfaces coact with an exterior surface of the wings to cause pivotally downward movement of the wings to draw them up to the needle portion along its axis, when the movable member is moved from the upper position to the lower position, and wherein:

the needle base has a groove extending perpendicular to the axis of the needle portion, the groove has a length along said axis and an upper section longitudinally delimited by lateral flanges, and the device further comprises a removable handle having proximal and distal ends, said distal end being engaged into the groove, below the upper flanges.

13. A hypodermic needle device comprising:

a needle having a portion adapted to be inserted into a body, said portion having a length along an axis and a distal sharp end and a proximal end, a needle base disposed over a segment of the needle at the proximal end of said needle portion, a needle portion shield comprising at least two generally flat wings having proximal and distal ends, at least two hinges, with one said hinge connecting the proximal end of each said wing with said needle base, a movable member having an axial opening therethrough at least partially delimited by generally flat surfaces, so as to be disposed over the wings along the axis of said needle portion, between upper and lower positions, wherein in the upper position, the movable member is above the hinges and in the lower position, the movable member is substantially at the distal end of the wings and its flat surfaces coact with an exterior surface of the wings to cause pivotally downward movement of the wings to draw them up to the needle portion along its axis, when the movable member is moved from the upper position to the lower position, and the movable element comprises rounded deflecting abutments which are located below the flat surfaces of the movable member and against which the exterior surface of the wings is urged for coacting therewith when the movable member is moved between the lower and upper positions.

14. A hypodermic needle device comprising:

a needle having a portion adapted to be inserted into a body through a receiving surface thereof, said portion having a length along an axis and a distal sharp end and a proximal end, a needle base disposed over a segment of the needle at the proximal end of said needle portion, the segment being bent there, a needle portion shield comprising at least two generally flat wings having proximal and distal ends, at least two hinges, with one said hinge connecting the proximal end of each said wing with said needle base, a movable member having an axial opening therethrough, so as to be disposed over the wings along the axis of said needle portion, between upper and lower positions, the movable member having a generally flat shape in a plane essentially perpendicular to the axis of the needle portion, so that said needle portion is adapted to be engaged essentially perpendicular to the receiving surface of the body, wherein in the upper position, the movable member is above the hinges and in the lower position, the movable member is substantially at the distal end of the wings and coacts with an exterior surface of the wings to cause pivotally downward movement of the wings to draw them up to the needle portion along its axis when the movable member is moved from the upper to the lower position.

* * * * *